United States Patent
Igari et al.

(10) Patent No.: US 7,265,157 B1
(45) Date of Patent: Sep. 4, 2007

(54) SUSTAINED RELEASE COMPOSITIONS, PROCESS FOR PRODUCING THE SAME AND USE THEREOF

(75) Inventors: Yasutaka Igari, Kobe (JP); Yoshio Hata, Kayabe-gun (JP); Kazumichi Yamamoto, Kyoto (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1189 days.

(21) Appl. No.: 10/019,786

(22) PCT Filed: Jul. 13, 2000

(86) PCT No.: PCT/JP00/04683

§ 371 (c)(1),
(2), (4) Date: Jan. 4, 2002

(87) PCT Pub. No.: WO01/05380

PCT Pub. Date: Jan. 25, 2001

(30) Foreign Application Priority Data

Jul. 15, 1999 (JP) ................................ 11/201887

(51) Int. Cl.
*A61K 47/12* (2006.01)
*A61K 38/00* (2006.01)

(52) U.S. Cl. ................................ 514/772.1; 514/772.6; 514/2

(58) Field of Classification Search ............... None
See application file for complete search history.

(56) References Cited

U.S. PATENT DOCUMENTS 6,740,634 B1 * 5/2004 Saikawa et al. ............... 514/2
6,756,472 B1 * 6/2004 Hata et al. ................. 528/354

FOREIGN PATENT DOCUMENTS

| EP | 0 839 525 | | 5/1998 |
|---|---|---|---|
| JP | 11269094 A | * | 10/1999 |
| WO | 96/22786 | | 8/1996 |
| WO | 98/32423 | | 7/1998 |
| WO | 99/36099 | | 7/1999 |
| WO | 00/35990 | | 6/2000 |

OTHER PUBLICATIONS

"Uterine Fibroids." Encyclopedia of Medicine. Ed. Jacqueline L. Longe. Thomson Gale, 2002. eNotes.com. 2006. accessed Mar. 1, 2006, <http://health.enotes.com/medicine-encyclopedia/uterine-fibroids> 4 pages.*
"Early Puberty." A-Z guide. Alan Greene. Aug. 31, 2002. Accessed Mar. 1, 2006. <http:www.drgreene.com/21_1075.html> 2 pages.*
"Endometriosis." A-Z health guide. WebMD. last updated Aug. 8, 2005. Accessed Mar. 1, 2006. <http://www.webmd.com/hw/endometriosis/hw103168.asp> 1 page.*
Benign Prostatic Hyperplasia (BPH): A Patient's Guide. American Urological Association. 2003. 15 pages.*
Prostate Cancer Screening. A decision Guide. CDC. Feb. 2003. 17 pages.*
Breast Cancer. National Alliance for Hispanic Health. rev. Aug. 2004. 6 pages.*
English Translation of JP 11269094 A.*

* cited by examiner

*Primary Examiner*—Cecilia J. Tsang
*Assistant Examiner*—Andrew D. Kosar
(74) *Attorney, Agent, or Firm*—Foley & Lardner LLP

(57) ABSTRACT

Sustained release compositions containing a physiologically active substance or its salt, hydroxynaphthoic acid or its salt and a lactic acid-glycolic polymer or its salt, wherein the product of the weight-average molecular weight of the lactic acid-glycolic acid polymer by the amount (µmol) of the terminal carboxyl group per unit mass (g) of the lactic acid-glycolic acid polymer is from 1,200,000 to 3,000,000 (inclusive); and their production; medicaments containing these sustained release compositions, etc.

4 Claims, No Drawings

SUSTAINED RELEASE COMPOSITIONS, PROCESS FOR PRODUCING THE SAME AND USE THEREOF

FIELD OF THE INVENTION

The present invention relates to a sustained release formulation of a pharmacologically active substance and a method for producing the same.

BACKGROUND OF THE INVENTION

JP-A-7-97334 discloses a sustained release formulation consisting of a physiologically active peptide or its salt and a biodegradable polymer having a terminal free carboxyl group as well as a method for producing the same.

Each of GB2209937, GB2234169, GB2234896, GB2257909 and EP626170A2 discloses a composition comprising as a base a biodegradable polymer containing a water-insoluble salt such as a pamoate of a peptide or a protein prepared separately as well as a method for producing the same.

WO95/15767 discloses an embonate (pamoate) of cetrorelix (LH-RH antagonist) and a method for producing the same, and describes that this pamoate, even when enclosed in a biodegradable polymer, exhibits the peptide-releasing performance equivalent to the pamoate which exists independently.

DISCLOSURE OF THE INVENTION

There is provided a novel composition containing a physiologically active substance at a high concentration whose excessive initial release is suppressed whereby accomplishing a stable releasing rate over a prolonged period (preferably about 6 months or longer).

The present inventors made an effort to solve the problems described above and finally discovered that by allowing a physiologically active substance and a hydroxynaphthoic acid to coexist upon forming a composition the physiologically active substance can be introduced at a high concentration into the composition; that further by enclosing these two components into a lactic acid-glycolic acid polymer the physiologically active substance can be released at a releasing rate different from the rate at which the physiologically active substance is released from a composition formed from the physiologically active substance and the hydroxynaphthoic acid prepared in the absence of the lactic acid-glycolic acid polymer; that this releasing rate can be controlled by selecting the characteristics of the lactic acid-glycolic acid polymer and the amount of the hydroxynaphthoic acid; that an initial excessive release can surely be suppressed even at a high concentration whereby accomplishing a sustained release over an extremely prolonged period (preferably about 6 months or longer); and also that by employing a lactic acid-glycolic acid polymer whose weight average molecular weight multiplied by the amount (μmol) of the terminal carboxyl group per unit mass (g) of the lactic acid-glycolic acid polymer is 1,200,000 to 3,000,000 (inclusive) a further satisfactory sustained release formulation can be provided. As a result of a further effort, the present invention was completed.

Thus, the present invention provides:

(1) a sustained release composition comprising a pharmacologically active substance or its salt, a hydroxynaphthoic acid or its salt and a lactic acid-glycolic acid polymer or its salt, wherein the product of the weight average molecular weight of said lactic acid-glycolic acid polymer by the amount (μmol) of the terminal carboxyl group per unit mass (g) of said lactic acid-glycolic acid polymer is 1,200,000 to 3,000,000 (inclusive);

(2) the sustained release composition according to the above-mentioned (1), wherein the pharmacologically active substance is a physiologically active peptide;

(3) the sustained release composition according to the above-mentioned (1), wherein the pharmacologically active substance is an LH-RH derivative;

(4) the sustained release composition according to the above-mentioned (1), wherein the hydroxynaphthoic acid is 1-hydroxy-2-naphthoic acid or 3-hydroxy-2-naphthoic acid;

(5) the sustained release composition according to the above-mentioned (1), wherein the hydroxynaphthoic acid is 1-hydroxy-2-naphthoic acid.

(6) the sustained release composition according to the above-mentioned (1) wherein the % molar ratio between lactic acid and glycolic acid is 100/0 to 40/60;

(7) the sustained release composition according to the above-mentioned (1), wherein the % molar ratio between lactic acid and glycolic acid is 100/0;

(8) the sustained release composition according to the above-mentioned (1), wherein the weight average molecular weight of the polymer is about 3,000 to about 100,000;

(9) the sustained release composition according to the above-mentioned (8), wherein the weight average molecular weight is about 20,000 to about 50,000;

(10) the sustained release composition according to the above-mentioned (3), wherein the LH-RH derivative is a peptide represented by Formula:

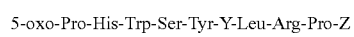

5-oxo-Pro-His-Trp-Ser-Tyr-Y-Leu-Arg-Pro-Z wherein Y denotes DLeu, DAla, DTrp, DSer(tBu), D2Nal or DHis(ImBzl), and Z denotes $NH-C_2H_5$ or $Gly-NH_2$;

(11) the sustained release composition according to the above-mentioned (1), wherein the amount (μmol) of the terminal carboxyl group of the polymer is 50 to 90 μmol per unit mass (g) of the polymer;

(12) the sustained release composition according to the above-mentioned (3), wherein the molar ratio between the hydroxynaphthoic acid or its salt and the LH-RH derivative or its salt is 3:4 to 4:3;

(13) the sustained release composition according to the above-mentioned (3) which contains the LH-RH derivative or its salt in an amount of 12% by weight to 24% by weight based on the sustained release composition;

(14) the sustained release composition according to the above-mentioned (1), wherein the physiologically active substance or its salt is a slightly water-soluble or water-soluble substance;

(15) the sustained release composition according to the above-mentioned (1) which is a formulation for injection;

(16) a method for producing a sustained release composition according to the above-mentioned (1) which comprises removing a solvent from a mixture of a pharmacologically active substance or its salt, a lactic acid-glycolic acid polymer or its salt and a hydroxynaphthoic acid or its salt;

(17) the method according to the above-mentioned (16) which comprises mixing the pharmacologically active substance or its salt with a solution of the lactic acid-glycolic acid polymer or its salt and the hydroxynaphthoic acid or its salt in an organic solvent, dispersing the mixture, and then removing the organic solvent;

(18) the method according to the above-mentioned (16), wherein the pharmacologically active substance or its salt is an aqueous solution containing the pharmacologically active substance or its salt;

(19) the method according to the above-mentioned (16), wherein the salt of the pharmacologically active substance is a salt with a free base or acid;

(20) a medicament comprising a sustained release composition according to the above-mentioned (1);

(21) a prophylactic or therapeutic agent against prostate cancer, prostate hyperplasia, endometriosis, hysteromyoma, metrofibroma, precocious puberty, dysmenorrhea or mammary cancer or an contraceptive containing a sustained release composition according to the above-mentioned (3);

(22) the sustained release composition according to the above-mentioned (1), wherein the pharmacologically active substance or its salt is released over a period of at least 6 months or longer; and

(23) a sustained release composition comprising a pharmacologically active substance or its salt, 1-hydroxy-2-naphthoic acid or its salt and a biodegradable polymer or its salt.

Furthermore, the invention provides:

(24) a method for producing a sustained release composition according to the above-mentioned (16) which comprises producing a w/o emulsion having as an inner aqueous phase a liquid containing the physiologically active substance or its salt and as an oil phase a solution containing the lactic acid-glycolic acid or its salt and the hydroxynaphthoic acid or its salt followed by removing a solvent;

(25) a method for producing a sustained release composition according to the above-mentioned (16) which comprises producing a w/o emulsion having as an inner aqueous phase a liquid containing the hydroxynaphthoic acid or its salt and as an oil phase a solution containing the physiologically active substance or its salt and the lactic acid-glycolic acid or its salt followed by removing a solvent;

(26) a method for producing a sustained release composition according to the above-mentioned (16) which comprises mixing the pharmacologically active substance or its salt with the hydroxynaphthoic acid or its salt, dissolving the mixture, and then removing the organic solvent; and

(27) a method for producing a sustained release composition according to any of the above-mentioned (24) to (26) wherein the process for removing the solvent is a in-water drying method.

While a physiologically active substance employed in the present invention is not limited particularly as long as it is pharmaceutically useful, it may be a non-peptide compound or a peptide compound. A non-peptide compound may for example be an agonist, an antagonist and a compound having an inhibitory effect on an enzyme. An example of a preferred peptide compound is a physiologically active peptide having a molecular weight of about 300 to about 40,000, preferably about 400 to about 30,000, more preferably about 500 to about 20,000.

Such physiologically active peptide may for example be luteinization hormone-releasing hormone (LH-RH), insulin, somatostatin, growth hormone, growth hormone-releasing hormone (GH-RH), prolactin, erythropoietin, adrenocortical hormone, melanocyte-stimulating hormone, thyroid hormone-releasing hormone, thyroid-stimulating hormone, loteinization hormone, follicle-stimulating hormone, vasopressin, oxytocin, calcitonin, gastrin, serectin, pancreozymin, cholecystokinin, angiotensin, human placental lactogen, human chorionic gonadotropin, enkephalin, endorphin, L-tyrosil L-arginine "KYOTORPHIN", tuftsin, thymopoictin, thymosin, "THYMOTHYMRIN", thymic humoral factor, blood thymic factor, tumor necrosis factor, colony-inducing factor, motilin, "DEINORPHINE", bombesin, neurotensin, cerulcin, bradykinin, atrial natrumetic factor, nerve growth factor, cell growth factor, neurotrophic factor, endothelin-antagonizing peptide and their derivative as well as their fragments and derivative thereof.

In the present invention, a physiologically active substance may be employed as it is or as a pharmaceutically acceptable salt thereof.

A salt of a physiologically active substance having a basic group such as an amino group may for example be a salt with an inorganic acid (referred to also as an inorganic free acid) (e.g., carbonic acid, bicarbonic acid, hydrochloric acid, sulfuric acid, nitric acid, boric acid and the like) and with an organic acid (referred to also as an organic free acid) (e.g., succinic acid, acetic acid, propionic acid, trofluoroacetic acid and the like).

A salt of a physiologically active substance having an acidic group such as a carboxyl group may for example be a salt with an inorganic base (referred to also as an inorganic free base) (e.g., an alkaline metal such as sodium and potassium, an alkaline earth metal such as calcium and magnesium) or with an organic base (referred to also as an inorganic free base) (e.g., an organic amine such as triethylamine, a basic amino acid such as arginine). A physiologically active peptide may form a metal complex compound (e.g., copper complex, zinc complex and the like).

A preferred example of such physiologically active peptide is an LH-RH derivative or its salt which is useful for treating a hormone-dependent disease, especially a sex hormone-dependent cancer (e.g., prostate cancer, uterine cancer, mammary cancer, pituitary cancer and the like), a sex hormone-dependent disease such as prostate hyperplasia, endometriosis, hysteromyoma, precocious puberty, dysmenorrhea, amenorrhea, premenstrual syndrome, multilocular ovarian syndrome and the like, and useful as a contraceptive (or against infertility when utilizing a rebound effect after discontinuation). Also exemplified is an LH-RH derivative or its salt which is useful for treating a benign or malignant tumor which is not sex hormone-dependent but is LH-RH sensitive.

Typically, an LH-RH derivative or its salt may for example be the peptides described in Treatment with GnRH analogs: Controvesies and perspectives, The Parthenon Publishing Group Ltd., (1996), JP-W-3-503165, JP-A-3-101695, 7-97334 and 8-259460.

An LH-RH derivative may for example be an LH-RH agonist or an LH-RH antagonist, the latter may for example be a pharmacologically active peptide represented by Formula [I]:

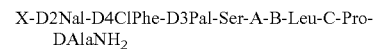

Wherein X denotes N(4H2-furoyl)Gly or NAc, A denotes a residue selected from NMeTyr, Tyr, Aph(Atz) and NMeAph (Atz), B denotes a residue selected from DLys(Nic), DCit, DLys(AzaglyNic), DLys(AzaglyFur), DhArg(Et$_2$), DAph (Atz) and DhCi, and C denotes Lys(Nisp), Arg or hArg(Et$_2$) or its salt.

An LH-RH agonist may for example be a pharmacologically active peptide represented by Formula [II]:

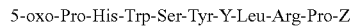
5-oxo-Pro-His-Trp-Ser-Tyr-Y-Leu-Arg-Pro-Z wherein Y denotes a residue selected from DLeu, DAla, DTrp, DSer(tBu), D2Nal and DHis(ImBzl), and Z denotes NH—C$_2$H$_5$ or Gly-NH$_2$ or its salt. One preferred especially is a peptide wherein Y is DLeu, Z is NH—C$_2$H$_5$ (i.e., a peptide represented by 5-oxo-Pro-His-Trp-Ser-Tyr-DLeu-Leu-Arg-Pro-NH—C$_2$H$_5$).

Any of these peptides can be produced by a method described in the foregoing references and specifications as well as a method in accordance therewith.

Abbreviations employed herein are listed below.

| Abbreviation | Name |
| --- | --- |
| N(4H2-furoyl)Gly: | N-tetrahydrofuroyl glycine residue |
| NAc: | N-acetyl group |
| D2Nal: | D-3-(2-naphthyl)alanine residue |
| D4ClPhe: | D-3-(4-chloro)phenylalanine residue |
| D3Pal: | D-3-(3-pyridyl)alanine residue |
| NMeTyr: | N-methyltyrosine residue |
| Aph(Atz): | N-[5'-(3'-amino-1'H-1',2',4'-triazolyl)]-phenylalanine residue |
| NmeAph(Atz): | N-methyl-[5'-(3'-amino-1'H-1',2',4'-triazolyl)]phenylalanine residue |
| DLys(Nic): | D-(e-N-nicotinoyl)lysine residue |
| Dcit: | D-citrulline residue |
| DLys(AzaglyNic): | D-(azaglycylnicotinoyl)lysine residue |
| DLys(AzaglyFur): | D-(azaglycylfuranyl)lysine residue |
| DhArg(Et$_2$): | D-(N,N'-diethyl)homoarginine residue |
| Daph(Atz): | D-N-[5'-(3'-amino-1'H-1',2',4'-triazolyl)]phenylalanine residue |
| DhCi: | D-homocitrulline residue |
| Lys(Nisp): | (e-N-isopropyl)lysine residue |
| hArg(Et$_2$): | (N,N'-diethyl)homoarginine residue |
| DSer(tBu): | O-tert-butyl-D-serine |
| Dhis(ImBzl): | N$^{im}$-benzyl-D-histidine |

Otherwise, an amino acid, when designated as an abbreviation, is represented as found in IUPAC-IUB Commission on Biochemical Nomenclature, European Journal of Biochemistry, Vol. 138, page 9 to 37 (1984) or as customary in the art, and an amino acid, even when optical isomers thereof exist, means an L form unless otherwise specified.

A hydroxynaphthoic acid employed in the invention is a naphthalene to which one hydroxyl group and one carboxyl group were bound on different carbon atoms. Accordingly, there were 14 isomers in total which differ from each other in the position of the hydroxyl group in relation to each of the 1-position and the 2-position at which the carboxyl group is bound to the naphthalene ring. The invention may employ any of these isomers as well as a mixture thereof at any ratio. As described below, one having a higher acid dissociation constant is preferable, or one having a lower pKa (pKa=−log 10 Ka wherein Ka is an acid dissociation constant is preferable. A slightly water-soluble isomer is preferable.

One also preferred is an isomer which is soluble in an alcohol (for example, ethanol and methanol). The expression "soluble in an alcohol" means that the solubility, for example in methanol, is 10 g/L or higher.

While the pKa of 3-hydroxy-2-naphthoic acid (pKa=2.708, KAGAKUBINRAN, II, NIPPON KAGAKU-KAI, Published on Sep. 25, 1969) is the only known pKa among hydroxynaphthoic acid isomers, a comparison of the pKa between the three isomers of hydroxybenzoic acid serves to give a useful information. Thus, the pKas of m-hydroxybenzoic acid and p-hydroxybenzoic acid are 4 or higher, while the pKa of o-hydroxybenzoic acid (salicylic acid) is far lower (=2.754). Accordingly, 3-hydroxy-2-naphthoic acid, 1-hydroxy-2-naphthoic acid and 2-hydroxy-1-naphthoic acid each having a carboxyl group and a hydroxyl group bound to the adjacent carbon atoms in the naphthalene ring are preferred among the 14 isomers described above.

A hydroxynaphthoic acid may be a salt. Such salt may for example be a salt with an inorganic base (e.g., an alkaline metal such as sodium and potassium, an alkaline earth metal such as calcium and magnesium), with an organic base (e.g., an organic amine such as triethylamine, a basic amino acid such as arginine), or with a transition metal (e.g., zinc, iron, copper) as well as a complex salt.

An example of a method for producing a hydroxynaphthoate of a pharmaceutically active substance of the invention is described below.

(1) A solution of a hydroxynaphthoic acid in a hydrated organic solvent is loaded onto and adsorbed by a weakly basic ion exchange column until saturation. Subsequently, the hydrated organic solvent is loaded to remove excessive hydroxynaphthoic acid and then a solution of a physiologically active substance or its salt in a hydrated organic solvent is loaded to effect an ion exchange, and the resultant effluent is made free of the solvent. Such hydrated organic solvent contains as an organic solvent an alcohol (e.g., methanol, ethanol), acetonitrile, tetrahydrofuran, dimethylformamide and the like. A method for removing the solvent to precipitate a salt may be a method known per se or a method in accordance therewith. For example, the solvent is evaporated off with adjusting the vacuum level using a rotary evaporator.

(2) The exchange ion of a strongly basic ion exchange column has previously been replaced with a hydroxide ion and then is loaded with a solution of a physiologically active substance or its salt in a hydrated organic solvent whereby exchanging the basic groups into the hydroxides. The recovered effluent was used to dissolve a hydroxynaphthoic acid in an amount less than the equivalent, concentrated to precipitate a salt, which is dried if necessary after washing with water.

Since a hydroxynaphthoate of a physiologically active substance is slightly water-soluble although the solubility may vary depending on the physiologically active substance employed, it can be used as a sustained release formulation utilizing the sustained releasing ability of the physiologically active peptide salt itself or it can further be formulated into a sustained release composition.

A lactic acid-glycolic acid polymer employed in the invention is a lactic acid-glycolic acid polymer whose weight average molecular weight multiplied by the amount (μmol) of the terminal carboxyl group per unit mass (g) of the lactic acid-glycolic acid polymer is 1,200,000 to 3,000,000 (inclusive), preferably 1,500,000 to 2,600,000 (inclusive), with one having a terminal free carboxyl group being employed preferably.

A lactic acid-glycolic acid polymer may be in the form of a salt. Such salt may for example be a salt with an inorganic base (e.g., an alkaline metal such as sodium and potassium, an alkaline earth metal such as calcium and magnesium), with an organic base (e.g., an organic amine such as triethylamine, a basic amino acid such as arginine), or with a transition metal (e.g., zinc, iron, copper) as well as a complex salt.

Such polymer has a % molar ratio between lactic acid and glycolic acid ranging preferably from about 100/0 to about 40/60, more preferably from about 100/0 to about 50/50. A lactic acid homopolymer whose % molar ratio is 100/0 is also employed preferably.

The optical isomer ratio of lactic acid which is one of the least repeating units of "lactic acid-glycolic acid polymer" described above, when represented as D-form/L-form (% mol/mol), is preferably about 75/25 to about 25/75. Those having a ratio of D-form/L-form (% mol/mol) especially of about 60/40 to about 30/70 are employed frequently.

The weight average molecular weight of "lactic acid-glycolic acid polymer" described above is usually about 3,000 to about 100,000, preferably about 3,000 to about 60,000, more preferably about 3,000 to about 50,000, especially about 20,000 to about 50,000.

A lactic acid-glycolic acid polymer of the invention may for example be a polymer having a weight average molecular weight multiplied by the amount ($\mu$mol) of the terminal carboxyl group per unit mass (g) of the lactic acid-glycolic acid polymer of 1,200,000 to 3,000,000 (inclusive), more preferably a polymer having a weight average molecular weight multiplied by the amount ($\mu$mol) of the terminal carboxyl group per unit mass (g) of the lactic acid-glycolic acid polymer of 1,500,000 to 2,600,000 (inclusive).

The polydispersity (weight average molecular weight/number average molecular weight) is usually about 1.2 to about 4.0, preferably about 1.5 to about 3.5, more preferably about 1.7 to about 3.0.

The amount of the free carboxyl group of "lactic acid-glycolic acid polymer" described above per unit mass (g) of the polymer is usually about 20 to about 1000 $\mu$mol, more preferably about 40 to about 1000 $\mu$mol. A further preferable amount is about 40 to about 95 $\mu$mol, especially about 50 to about 90 $\mu$mol.

Preferred examples are:

(1) a lactic acid-glycolic acid polymer whose weight average molecular weight is about 3,000 to about 100,000 and whose weight average molecular weight multiplied by the amount ($\mu$mol) of the terminal carboxyl group per unit mass (g) of the lactic acid-glycolic acid polymer is 1,200,000 to 3,000,000 (inclusive);

(2) a lactic acid-glycolic acid polymer whose weight average molecular weight is about 3,000 to about 60,000 and whose weight average molecular weight multiplied by the amount ($\mu$mol) of the terminal carboxyl group per unit mass (g) of the lactic acid-glycolic acid polymer is 1,200,000 to 3,000,000 (inclusive);

(3) a lactic acid-glycolic acid polymer whose weight average molecular weight is about 3,000 to about 50,000 and whose weight average molecular weight multiplied by the amount ($\mu$mol) of the terminal carboxyl group per unit mass (g) of the lactic acid-glycolic acid polymer is 1,200,000 to 3,000,000 (inclusive);

(4) a lactic acid-glycolic acid polymer whose weight average molecular weight is about 20,000 to about 50,000 and whose weight average molecular weight multiplied by the amount ($\mu$mol) of the terminal carboxyl group per unit mass (g) of the lactic acid-glycolic acid polymer is 1,200,000 to 3,000,000 (inclusive);

(5) a lactic acid-glycolic acid polymer whose amount ($\mu$mol) of the terminal carboxyl group per unit mass (g) of the lactic acid-glycolic acid polymer is about 20 to about 1000 $\mu$mol and whose weight average molecular weight multiplied by the amount ($\mu$mol) of the terminal carboxyl group per unit mass (g) of the lactic acid-glycolic acid polymer is 1,200,000 to 3,000,000 (inclusive);

(6) a lactic acid-glycolic acid polymer whose amount ($\mu$mol) of the terminal carboxyl group per unit mass (g) of the lactic acid-glycolic acid polymer is about 40 to about 1000 $\mu$mol and whose weight average molecular weight multiplied by the amount ($\mu$mol) of the terminal carboxyl group per unit mass (g) of the lactic acid-glycolic acid polymer is 1,200,000 to 3,000,000 (inclusive);

(7) a lactic acid-glycolic acid polymer [1] whose weight average molecular weight is about 3,000 to about 100,000, [2] whose amount ($\mu$mol) of the terminal carboxyl group per unit mass (g) of the lactic acid-glycolic acid polymer is about 20 to about 1000 $\mu$mol and [3] whose weight average molecular weight multiplied by the amount ($\mu$mol) of the terminal carboxyl group per unit mass (g) of the lactic acid-glycolic acid polymer is 1,200,000 to 3,000,000 (inclusive);

(8) a lactic acid-glycolic acid polymer [1] whose weight average molecular weight is about 3,000 to about 100,000, [2] whose amount ($\mu$mol) of the terminal carboxyl group per unit mass (g) of the lactic acid-glycolic acid polymer is about 40 to about 1000 $\mu$mol and [3] whose weight average molecular weight multiplied by the amount ($\mu$mol) of the terminal carboxyl group per unit mass (g) of the lactic acid-glycolic acid polymer is 1,200,000 to 3,000,000 (inclusive);

(9) a lactic acid-glycolic acid polymer [1] whose weight average molecular weight is about 3,000 to about 60,000, [2] whose amount ($\mu$mol) of the terminal carboxyl group per unit mass (g) of the lactic acid-glycolic acid polymer is about 20 to about 1000 $\mu$mol and [3] whose weight average molecular weight multiplied by the amount ($\mu$mol) of the terminal carboxyl group per unit mass (g) of the lactic acid-glycolic acid polymer is 1,200,000 to 3,000,000 (inclusive);

(10) a lactic acid-glycolic acid polymer [1] whose weight average molecular weight is about 3,000 to about 60,000, [2] whose amount ($\mu$mol) of the terminal carboxyl group per unit mass (g) of the lactic acid-glycolic acid polymer is about 40 to about 1000 $\mu$mol and [3] whose weight average molecular weight multiplied by the amount ($\mu$mol) of the terminal carboxyl group per unit mass (g) of the lactic acid-glycolic acid polymer is 1,200,000 to 3,000,000 (inclusive);

(11) a lactic acid-glycolic acid polymer [1] whose weight average molecular weight is about 3,000 to about 50,000, [2] whose amount ($\mu$mol) of the terminal carboxyl group per unit mass (g) of the lactic acid-glycolic acid polymer is about 20 to about 1000 $\mu$mol and [3] whose weight average molecular weight multiplied by the amount ($\mu$mol) of the terminal carboxyl group per unit mass (g) of the lactic acid-glycolic acid polymer is 1,200,000 to 3,000,000 (inclusive);

(12) a lactic acid-glycolic acid polymer [1] whose weight average molecular weight is about 3,000 to about 50,000, [2] whose amount ($\mu$mol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,200,000 to 3,000,000 (inclusive);

(13) a lactic acid-glycolic acid polymer [1] whose weight average molecular weight is about 20,000 to about 50,000, [2] whose amount (μmol) of the terminal carboxyl group per unit mass (g) of the lactic acid-glycolic acid polymer is about 20 to about 1000 μmol and [3] whose weight average molecular weight multiplied by the amount (μmol) of the terminal carboxyl group per unit mass (g) of the lactic acid-glycolic acid polymer is 1,200,000 to 3,000,000 (inclusive); and

(14) a lactic acid-glycolic acid polymer [1] whose weight average molecular weight is about 20,000 to about 50,000, [2] whose amount (μmol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,200,000 to 3,000,000 (inclusive).

More preferred example are:

(15) a lactic acid-glycolic acid polymer [1] whose weight average molecular weight is about 3,000 to about 100,000 and [2] whose weight average molecular weight multiplied by the amount (μmol) of the terminal carboxyl group per unit mass (g) of the lactic acid-glycolic acid polymer is 1,500,000 to 2,600,000 (inclusive);

(16) a lactic acid-glycolic acid polymer [1] whose weight average molecular weight is about 3,000 to about 60,000 and [2] whose weight average molecular weight multiplied by the amount (μmol) of the terminal carboxyl group per unit mass (g) of the lactic acid-glycolic acid polymer is 1,500,000 to 2,600,000 (inclusive);

(17) a lactic acid-glycolic acid polymer [1] whose weight average molecular weight is about 3,000 to about 50,000 and [2] whose weight average molecular weight multiplied by the amount (μmol) of the terminal carboxyl group per unit mass (g) of the lactic acid-glycolic acid polymer is 1,500,000 to 2,600,000 (inclusive);

(18) a lactic acid-glycolic acid polymer [1] whose weight average molecular weight is about 20,000 to about 50,000 and [2] whose weight average molecular weight multiplied by the amount (μmol) of the terminal carboxyl group per unit mass (g) of the lactic acid-glycolic acid polymer is 1,500,000 to 2,600,000 (inclusive);

(19) a lactic acid-glycolic acid polymer [1] whose amount (μmol) of the terminal carboxyl group per unit mass (g) of the lactic acid-glycolic acid polymer is about 20 to about 1000 μmol and [2] whose weight average molecular weight multiplied by the amount (μmol) of the terminal carboxyl group per unit mass (g) of the lactic acid-glycolic acid polymer is 1,500,000 to 2,600,000 (inclusive);

(20) a lactic acid-glycolic acid polymer [1] whose amount (μmol) of the terminal carboxyl group per unit mass (g) of the lactic acid-glycolic acid polymer is about 40 to about 1000 μmol and [2] whose weight average molecular weight multiplied by the amount (μmol) of the terminal carboxyl group per unit mass (g) of the lactic acid-glycolic acid polymer is 1,500,000 to 2,600,000 (inclusive);

(21) a lactic acid-glycolic acid polymer [1] whose weight average molecular weight is about 3,000 to about 100,000 and [2] whose amount (μmol) of the terminal carboxyl group per unit mass (g) of the lactic acid-glycolic acid polymer is about 20 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(22) a lactic acid-glycolic acid polymer [1] whose weight average molecular weight is about 3,000 to about 100,000 and [2] whose amount (μmol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(23) a lactic acid-glycolic acid polymer [1] whose weight average molecular weight is about 3,000 to about 60,000 and [2] whose amount (μmol) of the terminal carboxyl group per unit mass (g) of the lactic acid-glycolic acid polymer is about 20 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(24) a lactic acid-glycolic acid polymer [1] whose weight average molecular weight is about 3,000 to about 60,000 and [2] whose amount (μmol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(25) a lactic acid-glycolic acid polymer [1] whose weight average molecular weight is about 3,000 to about 50,000 and [2] whose amount (μmol) of the terminal carboxyl group per unit mass (g) of the lactic acid-glycolic acid polymer is about 20 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(26) a lactic acid-glycolic acid polymer [1] whose weight average molecular weight is about 3,000 to about 50,000 and [2] whose amount (μmol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive);

(27) a lactic acid-glycolic acid polymer [1] whose weight average molecular weight is about 20,000 to about 50,000 and [2] whose amount (μmol) of the terminal carboxyl group per unit mass (g) of the lactic acid-glycolic acid polymer is about 20 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive); and,

(28) a lactic acid-glycolic acid polymer [1] whose weight average molecular weight is about 20,000 to about 50,000 and [2] whose amount (μmol) of the terminal carboxyl group per unit mass (g) of the lactic acid-glycolic acid polymer is about 40 to about 1000 μmol and [3] whose weight average molecular weight multiplied by the amount (μmol) of the terminal carboxyl group per unit mass (g) of the lactic acid-glycolic acid polymer is 1,500,000 to 2,600,000 (inclusive).

A weight average molecular weight, a number average molecular weight and a polydispersity mean a molecular weight as polystyrene determined by a gel permeation chromatography (GPC) using as standards 15 monodisperse polystyrenes whose weight average molecular weights are 1,110,000, 707,000, 455,645, 354,000, 189,000, 156,055, 98, 900, 66,437, 37,200, 17,100, 9,830, 5,870, 2,500, 1,303 and 504 and a polydispersity calculated therefrom. The determination is performed using a high speed GPC instrument (TOSO, HLC-8120GPC, detection by differential refractive index) together with a GPC column KF804Lx2 (SHOW A DENKO) and chloroform as a mobile phase. The flow rate is 1 ml/min.

An amount of a free carboxyl group mentioned here means an amount determined by a labeling method (hereinafter referred to as a labeling method-based carboxyl group level). Typically, in the case of a polylactic acid, W mg of the polylactic acid is dissolved in 2 ml of a mixture of 5N hydrochloric acid/acetonitrile (v/v=4/96) and combined with 2 ml of a 0.01 M solution of o-nitrophenylhydrazine hydrochloride (ONPH) (5N hydrochloric acid/acetonitrile/ethanol=1.02/35/15) and 2 ml of a 0.15M solution of 1-ethyl-3-(3-dimethylaminopropyl)-carbodiimide hydrochloride (pyridine/ethanol=4 v/96 v), and after allowing the mixture to react at 40° C. for 30 minutes and then the solvent is distilled off. The residue is washed with water (4 times), dissolved in 2 ml of acetonitrile, combined with 1 ml of a 0.5 mol/L ethanolic solution of potassium hydroxide, and allowed to react at 60° C. for 30 minutes. The reaction mixture is diluted with a 1.5 N aqueous solution of sodium hydroxide to make Y ml, which is examined for the absorbance at 544 nm A(/cm) using a 1.5 N aqueous solution of sodium hydroxide as a reference standard. On the other hand, a n aqueous solution of DL-lactic acid is used as a standard to examine for its free carboxyl group C mol/L by means of an alkali titration, and subjected to an ONPH labeling method to convert into DL-lactic acid hydrazide, which is then examined for the absorbance at 544 nm B(/cm), based on which the molar amount of the free carboxyl group per unit mass)g) of the polymer is calculated in accordance with the following equation.

[COOH]=(mol/g)=(AYC)/(WB)

This "amount of the carboxyl group" can be obtained also by dissolving a lactic acid-glycolic acid polymer in a solvent mixture of toluene-acetone-methanol and titrating the resultant solution for the carboxyl group with an alcoholic solution of potassium hydroxide using phenolphthalein as an indicator (hereinafter a value obtained by this method is referred to as "alkali titration-based carboxyl group level").

Since the rate at which a lactic acid-glycolic acid polymer is degraded and disappears is reduced usually at a reduced ratio of glycolic acid although it may vary greatly depending on the copolymer composition, the molecular weight or the free carboxyl group level, it is possible to prolong the release duration by means of reducing the glycolic acid ratio or increasing the molecular weight simultaneously with reducing the free carboxyl group level.

Such "lactic acid-glycolic acid polymer" can be produced for example by a non-catalytic dehydrative condensation polymerization (JP-A-61-28521) from lactic acid and gly-colic acid or by a ring-opening polymerization from cyclic diester compounds such as lactides and glycolides (Encyclopedic Handbook of Biomaterials and Bioengineering Part A: Materials, Volume 2, Marcel Dekker, Inc, 1995). While a polymer obtained by the known ring-opening polymerization described above may sometimes be a polymer having no free carboxyl group at its terminal, such polymer can be converted into a polymer having a certain amount of the carboxyl group per unit mass for example by means of hydrolysis described in EP-A-0839525 prior to its use.

"Lactic acid-glycolic acid polymer having a terminal free carboxyl group" can readily be produced by a known method (for example, a non-catalytic dehydrative condensation polymerization, JP-A-61-28521) or by the following methods.

(1) First, a cyclic ester compound is subjected to a polymerization using a polymerization catalyst in the presence of a carboxyl-protected hydroxymonocarboxylic acid derivative (e.g. t-butyl D-lactate, benzyl L-lactate) or a carboxyl-protected hydroxydicarboxylic acid derivative (e.g., dibenzyl tartronate, di-t-butyl dihydroxyethylmalonate).

"Carboxyl-protected hydroxymonocarboxylic acid derivative" or "carboxyl-protected hydroxydicarboxylic acid derivative" mentioned above may for example be a hydroxycarboxylic acid derivative whose carboxyl group (—COOH) is amidated (—CONH$_2$) or esterified (—COOR), with a hydroxycarboxylic acid derivative whose carboxyl group (—COOH) is esterified (—COOR) being preferred.

R in an ester mentioned here may for example be a C$_{1-6}$ alkyl group such as methyl, ethyl, n-propyl, isopropyl, n-butyl and t-butyl, a C$_{3-8}$ cycloalkyl group such as cyclopentyl and cyclohexyl, a C$_{6-12}$ aryl group such as phenyl and α-naphthyl, a C$_{7-14}$ aralkyl group including a phenyl-C$_{1-2}$ alkyl group such as benzyl and phenethyl or an a-naphthyl-C$_{1-2}$ alkyl group such as α-naphthylmethyl. Among those listed above, a t-butyl group and a benzyl group are preferred.

"Cyclic ester compound" mentioned above may for example be a cyclic compound having at least one ester bond within the ring. Those which are exemplified typically are a cyclic monoester compound (lactone) and a cyclic diester compound (lactide).

"Cyclic monoester compound" mentioned above may for example be a 4-membered cyclic lactone (β-propiolactone, β-butyrolactone, β-isovalerolactone, β-caprolactone, β-isocaprolactone, β-methyl-β-valerolactone and the like), a 5-membered cyclic lactone (γ-butyrolactone, γ-valerolactone and the like), a 6-membered cyclic lactone (δ-valerolactone and the like), a 7-membered cyclic lactone (ε-caprolactone and the like), p-dioxanone, 1,5-dioxepan-2-one and the like.

"Cyclic diester compound" mentioned above may for example be a compound represented by Formula:

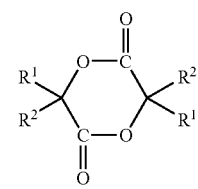

wherein R$^1$ and R$^2$ are the same or different and each denotes a hydrogen atom or a C$_{1-6}$ alkyl group such as methyl, ethyl, n-propyl, isopropyl, n-butyl and t-butyl), and a lactide wherein R$^1$ is a hydrogen atom and R$^2$ is a methyl group or each of R$^1$ and R$^2$ is a hydrogen atom.

Those exemplified typically are glycolide, L-lactide, D-lactide, DL-lactide, meso-lactide, 3-methyl-1,4-dioxane-2,5-dione (including optical isomers) and the like.

"Polymerization catalyst" mentioned above may for example be an organic tin-based catalyst (e.g., tin octylate, di-n-butyltin dilaurate, tetraphenyltin), an aluminum-based catalyst (e.g., triethylaluminum) and a zinc-based catalyst (e.g., diethylzinc).

Aluminum-based and zinc-based catalysts are preferred for the purpose of removing a solvent easily after a reaction, while a zinc-based catalyst is preferred for the purpose of ensuring the safety of residual catalyst if any.

A solvent for a polymerization catalyst is benzene, hexane, toluene and the like, with hexane and toluene being preferred especially.

"Polymerization method" may be a bulk polymerization in which a reactant is used as being melted or a solution polymerization in which a reactant is employed as being dissolved in a suitable solvent (for example, benzene, toluene, xylene, decalin, and dimethylformamide). A preferred solvent is toluene, xylene and the like. While the polymerization temperature is not limited particularly, a bulk polymerization may employ a temperature capable of melting a reactant at the initiation of the reaction or higher, usually 100 to 300° C., and a solution polymerization usually employs room temperature to 150° C. with using a condenser for reflux or a pressure-resistant reactor when the reaction temperature exceeds the boiling point of the reaction solution. While the polymerization time period may vary depending on the polymerization temperature, other reaction conditions and intended polymer characteristics, it may for example be 10 minutes to 72 hours. After the reaction, the reaction mixture is dissolved in a suitable solvent (for example, acetone, dichloromethane, chloroform), combined with an acid (for example, hydrochloric acid, acetic anhydride, trifluoroacetic acid) to terminate the polymerization, and then precipitated for example by mixing with a solvent which does not dissolve an intended product (for example, alcohol, water, ether, isopropyl ether) in accordance with a standard method, whereby isolating a lactic acid-glycolic acid polymer having a protected carboxyl group at its ω-terminal.

A polymerization method according to the invention employs a carboxyl-protected hydroxycarboxylic acid derivative (e.g., t-butyl D-lactate, benzyl L-lactate) or a carboxyl-protected hydroxydicarboxylic acid derivative (e.g., dibenzyl tartronate, di-t-butyl dihydroxyethylmalonate) instead of a protonic chain transfer agent such as methanol employed conventionally.

By using such carboxyl-protected hydroxycarboxylic acid derivative (e.g., t-butyl D-lactate, benzyl L-lactate) or carboxyl-protected hydroxydicarboxylic acid derivative (e.g., dibenzyl tartronate, di-t-butyl dihydroxyethylmalonate) as a protonic chain transfer agent, [1] it is possible to control the molecular weight on the basis of the input composition, and [2] a deprotection after the polymerization serves to make the carboxyl group free at the ω-terminal of the resultant lactic acid-glycolic acid polymer.

(2) Subsequently, a lactic acid-glycolic acid polymer having a protected carboxyl group at its ω-terminal obtained by the polymerization in above-mentioned (1) is deprotected to obtain an intended lactic acid-glycolic acid polymer having a free carboxyl group at its ω-terminal.

A protecting group can be deprotected by a method known per se. While the method may be any method as long as it can remove the protective group without affecting the ester bond of a poly(hydroxycarboxylic acid) adversely, it may typically be a reduction, an acid decomposition and the like.

A reduction method may for example be a catalytic hydrogenation using a catalyst (e.g., palladium on carbon, palladium black, platinum oxide), a reduction with sodium in a liquid ammonium and a reduction with dithiothreitol. In the case for example that a polymer having a carboxyl group protected by a benzyl group at its ω-terminal is hydrogenated catalytically, the polymer dissolved typically in ethyl acetate, dichloromethan, chloroform and the like is combined with a palladium on carbon, bubbled with hydrogen with stirring vigorously at room temperature for about 20 minutes to about 4 hours, whereby accomplishing deprotection.

An acid decomposition may for example be an acid decomposition using an inorganic acid (e.g., hydrogen fluoride, hydrogen bromide, hydrogen chloride) or an organic acid (e.g., trifluoroacetic acid, methanesulfonic acid, trifluoromethanesulfonic acid) as well as a mixture thereof. If necessary, the acid decomposition may be performed in the presence of a cation scavenger (e.g., anisol, phenol, thioanisol). In the case for example that a polymer having a carboxyl group protected by a t-butyl group at its ω-terminal is subjected to an acid decomposition, the polymer dissolved typically in dichloromethane, xylene, toluene and the like is combined with trifluoroacetic acid in an appropriate amount or the polymer is dissolved in trifluoroacetic acid, and then the mixture is stirred at room temperature for about 1 hour, whereby accomplishing deprotection.

Preferably, an acid decomposition may also be conducted immediately after a polymerization reaction, and in such case it serves also as a polymerization termination reaction.

Also if necessary, a lactic acid-glycolic acid polymer obtained by a deprotection described above can be subjected to an acid hydrolysis to adjust the weight average molecular weight, the number average molecular weight or the terminal carboxyl group level as intended. Typically, a method described in EP-A-0839525 or a method in accordance therewith may be employed.

A lactic acid-glycolic acid polymer obtained as described above can be used as a base for producing a sustained release formulation.

A polymer having a non-specific free carboxyl group at its terminal can be produced by a known method (for example, see WO94/15587).

Furthermore, a lactic acid-glycolic acid polymer whose terminal has been converted into a free carboxyl group by means of a chemical treatment after a ring-opening polymerization is available commercially for example from Boehringer Ingelheim KG.

A lactic acid-glycolic acid polymer may be present as a salt (such as those listed above), which can be produced for example by (a) a method in which a lactic acid-glycolic acid polymer having a carboxyl group described above dissolved in an organic solvent is combined with an aqueous solution containing an inorganic base (e.g., an alkaline metal such as sodium and potassium, an alkaline earth metal such as calcium and magnesium) or with an organic base (e.g., an organic amine such as triethylamine, a basic amino acid such as arginine) to effect an ion exchanging reaction, followed by an isolation of the polymer as a salt, (b) a method in which a weak acid salt of a base listed in above-mentioned (a) (for example, acetate and glycolate) is dissolved in a solution of a lactic acid-glycolic acid polymer having a carboxyl group described above in an organic solvent and then the lactic acid-glycolic acid polymer in the form of a salt is isolated, (c) a method in which a lactic acid-glycolic acid polymer having a carboxyl group described above dissolved in an organic solvent is combined with a weak acid salt (for example, acetate and glycolate) or an oxide of a transition metal (e.g., zinc, iron, copper) and then the lactic acid-glycolic acid polymer in the form of a salt is isolated.

While the weight ratio of a pharmacologically active substance in a composition of the invention may vary depending on the type of the pharmacologically active substance, the pharmacological effects desired and the duration thereof, it is about 0.001 to about 50% by weight, preferably about 0.02 to about 40% by weight, more preferably about 0.1 to about 30% by weight, most preferably 12 to 24% by weight in the case of a physiologically active peptide or its salt based on the total amount of the physiologically active substance or its salt, a hydroxynaphthoic acid or its salt and a lactic acid-glycolic acid polymer or its salt when latter three components are contained in a sustained release composition, and about 0.01 to about 80% by weight, preferably about 0.1 to about 50% by weight in the case of a non-peptide physiologically active substance or its salt. Similar ranges of the weight ratio are applicable even when a physiologically active substance and a hydroxynaphthoic acid are contained. In the case of a sustained release composition comprising a salt of a physiologically active peptide (designated here as (A)) with a hydroxynaphthoic acid (designated here as (B)), the weight ratio of (A) based on the total amount of (A)+(B) is usually about 5 to about 90% by weight, preferably about 10 to about 85% by weight, more preferably about 15 to about 80% by weight, especially about 30 to about 80% by weight.

In the case of a sustained release composition containing three components, namely, a physiologically active substance or its salt, a hydroxynaphthoic acid or its salt and a lactic acid-glycolic acid polymer or its salt, the amount of the hydroxynaphthoic acid or its salt per 1 mole of the physiologically active substance or its salt is about 1/2 to about 2 moles, preferably about 3/4 to about 4/3 moles, especially about 4/5 to about 6/5 moles.

A procedure for designing a composition of the invention is discussed below with referring to a sustained release composition containing three components, namely, a physiologically active substance, a hydroxynaphthoic acid and a lactic acid-glycolic acid polymer in which the physiologically active substance is a basic substance. In this case, the composition contains the physiological active substance as a base and the hydroxynaphthoic acid as an acid, each of which establishes its dissociation equilibrium in a hydrated state or in the presence of a trace amount of water at any time point during the production of the composition in any case that it is incorporated as a free form or a salt into the composition. Since a salt which a slightly water-soluble hydroxynaphthoic acid forms together with a physiologically active substance is considered to be slightly water-soluble although the solubility may vary depending on the physiologically active substance employed, the dissociation equilibrium serves favorably for the formation of such slightly water-soluble salt.

In order to produce a composition containing a basic physiologically active substance at a high concentration, it is preferable in view of the dissociation equilibrium discussed above to protonate almost all of the physiologically active substance to form a slightly water-soluble salt described above. For this purpose, it is preferable that a hydroxynaphthoic acid or its salt in an amount at least almost equivalent to the physiologically active substance or its salt is incorporated.

The mechanism by which a physiologically active substance contained in a composition is released sustainedly is then discussed below. The physiologically active substance has mostly been protonated and exists together with an accompanying counter ion in the composition described above. The counter ion is mainly a hydroxynaphthoic acid. After an administration of the composition to a living body, the lactic acid-glycolic acid polymer undergoes a degradation to form its oligomers and monomers, and each of the resultant oligomers (lactic acid-glycolic acid oligomers) and monomers (lactic acid or glycolic acid) surely has one carboxyl group, which can also serves as a counter ion for the physiologically active substance. While the physiologically active substance is released in a manner involving no transfer of an electric charge, i.e., it is released as a salt accompanied with a counter ion, transferable counter ion species may for example be hydroxynaphthoic acids, lactic acid-glycolic acid oligomers (having transferable molecular weights) and monomers (lactic acid or glycolic acid).

When two or more acids are present simultaneously, a salt with a strong acid is formed predominantly in general, although the predominance may vary depending on the ratio. With regard to the pKa of a hydroxynaphthoic acid, the pKa for example of 3-hydroxy-2-naphthoic acid is 2.708 (KA-GAKUBINRAN, II, NIPPON KAGAKUKAI, Published on Sep. 25, 1969). On the other hand, the pKa of the carboxyl group of a lactic acid-glycolic acid oligomer is not known, but it can be calculated from the pKa of lactic acid or glycolic acid (=3.86 or 3.83) in accordance with the principle that "the change in the free energy by the introduction of a substituent can be subjected to an approximation on the basis of addition rule". The contribution of a substituent to a dissociation constant was determined and can be utilized (Table 4.1, "pKa Prediction for Organic Acid and Bases", D. D. Perrin, B. Dempsey and E. P. Sergeant, 1981). The pKas of a hydroxyl group and an ester bond are represented as follows:

ΔpKa(OH)=−0.90

ΔpKa(ester bond)=−1.7.

Accordingly, the pKa of a carboxyl group in a lactic acid-glycolic acid oligomer, when taking the contribution of an ester bond which is closest to the dissociated group into consideration, is represented as follows:

pKa=pKa(lactic acid or glycolic acid)−ΔpKa(OH)+ΔpKa (ester bond)=3.06 or 3.03. Accordingly, a hydroxynaphthoic acid is an acid which is stronger than lactic acid (pKa=3.86), glycolic acid (pKa=3.83) and the lactic acid-glycolic acid oligomer (pLa=3.83), and thus it is possible that the salt of the hydroxynaphthoic acid and the physiologically active substance is formed predominantly in the composition described above and that the characteristics of the salt predominantly determines the sustained release profile of the physiologically active substance from the composition. A physiologically active substance employed here may for example be a physiologically active substance mentioned above.

In this context, the fact that the salt formed from the hydroxynaphthoic acid with the physiologically active substance is slightly water-soluble rather than water-insoluble serves favorably for the sustained release mechanism. Thus, since a predominant existence of a salt of the hydroxynaphthoic acid which is stronger than the lactic acid-glycolic acid oligomer and the monomers among transferable physiologically active substance salts at an early stage of the release as evident from the discussion on the acid dissociation constant described above allows the solubility and the tissue distribution performance of the salt to be determinant factors of a release rate of the physiologically active substance, the initial release pattern of the substance can be adjusted on the basis of the amount of the hydroxynaphthoic acid to be added. Subsequently, a decrease in the hydroxynaphthoic acid and an increase in the oligomers and the monomers formed as a result of the hydrolysis of the lactic acid-glycolic acid polymer leads to a gradual predominance of the release mechanism of the physiologically active substance whose counter ions are the oligomers and the monomers, whereby maintaining a stable release of the physiologically active substance even after the hydroxynaphthoic acid is depleted substantially from "composition" described above. An increased efficiency in incorporating the physiologically active substance during the manufacturing process of the sustained release composition and an ability of suppressing an initial excessive release after an administration of the physiologically active substance incorporated can similarly be explained.

Also explained similarly by the mechanism described above is a role of a hydroxynaphthoic acid in a sustained release composition containing a hydroxynaphthoate of a physiologically active peptide.

The term "water-insoluble" used here means that the mass of a substance dissolved in 1 L of a solution after stirring said substance at a temperature of 40° C. or lower in distilled water for 4 hours is 25 mg or less.

The term "slightly water-insoluble" used herein means that the mass described above is greater than 25 mg and not greater than 5 g. When the relevant substance is a salt of a physiologically active substance, then the mass of the physiologically active substance dissolved in the procedure described above is subjected to the definition described above.

While the morphology of a sustained release composition in the invention is not limited particularly, it is preferably a microparticle, especially a microsphere (also referred to as a microcapsule in the case of a sustained release composition containing a lactic acid-glycolic acid polymer). A microsphere mentioned here means an injectable spherical microparticle capable of being dispersed in a solution. The morphology can be verified for example by an observation using a scanning electron microscope.

A method for producing a an inventive sustained release composition comprising a pharmacologically active substance or its salt, a hydroxynaphthoic acid or its salt and a lactic acid-glycolic acid polymer or its salt is described below with exemplifying a microcapsule.

(I) In-Water Drying Method (i) O/W Method

In this method, a solution of a hydroxynaphthoic acid or its salt and a lactic acid-glycolic acid polymer or its salt in an organic solvent is prepared first. An organic solvent used for producing an inventive sustained release formulation preferably has a melting point of 120° C. or lower.

Such organic solvent may for example be a halogenated hydrocarbon (e.g., dichloromethane, chloroform, dichloroethane, trichloroethane, carbon tetrachloride), an ether (e.g., ethyl ether, isopropyl ether), a fatty acid ester (e.g., ethyl acetate, butyl acetate), an aromatic hydrocarbon (e.g., benzene, toluene, xylene), an alcohol (e.g., ethanol, methanol) as well as acetonitrile. As an organic solvent for a lactic acid-glycolic acid polymer or its salt, dichloromethane is especially preferred.

As an organic solvent for the hydroxynaphthoic acid or its salt, an alcohol or a mixture of an alcohol and a halogenated hydrocarbon is especially preferred.

The hydroxynaphthoic acid or its salt and the lactic acid-glycolic acid polymer or its salt may be dissolved separately and then mixed with each other, or the both may be dissolved in an organic solvent mixture at a certain ratio. Among the solvents, a mixture of a halogenated hydrocarbon and an alcohol is employed preferably, with a mixture of dichloromethane and ethanol being preferred particularly.

The ethanol content in an organic solvent mixture of dichloromethane and ethanol when using ethanol as an organic solvent to be mixed with dichloromethane is usually about 0.01 to about 50% (v/v), more preferably about 0.05 to about 40% (v/v), especially about 0.1 to about 30% (v/v).

While the concentration of the lactic acid-glycolic acid polymer in an organic solvent solution may vary depending on the molecular weight of the lactic acid-glycolic acid polymer and the type of the organic solvent, it is usually about 0.5 to about 70% by weight, more preferably about 1 to about 60% by weight, especially about 2 to about 50% by weight, when using dichloromethane as an organic solvent.

The concentration of the hydroxynaphthoic acid or its salt in an organic solvent, when using a mixture of dichloromethane and ethanol as an organic solvent, is usually about 0.01 to about 10% by weight, more preferably about 0.1 to about 5% by weight, especially about 0.5 to about 3% by weight.

To the solution of the hydroxynaphthoic acid or its salt and the lactic acid-glycolic acid polymer thus obtained, a pharmacologically active substance or its salt is added and dissolved or dispersed. Then, the resultant organic solvent solution containing a composition consisting of the pharmacologically active substance or its salt, the hydroxynaphthoic acid or its salt and the lactic acid-glycolic acid polymer is added to an aqueous phase to form an O(oil phase)/W (aqueous phase) emulsion, and then the solvent in the oil phase is evaporated or dispersed in the aqueous phase, whereby preparing a microcapsule. The volume of this aqueous phase is usually about 1 to about 10,000 times, more preferably about 5 to about 50,000 times, especially about 10 to about 2,000 times the volume of the oil phase.

The outer aqueous phase described above may contain an emulsifier. Such emulsifier may usually be any emulsifier capable of forming a stable O/W emulsion. One employed typically is an anionic surfactant (sodium oleate, sodium stearate, sodium laurylsulfate and the like), a nonionic surfactant (polyoxyethylene sorbitan fatty acid ester [polyoxyethylene 20 sorbitan monooleate sold under the trademark TWEEN® 80, polyoxyethylene sorbitan monostearate sold under the trademark TWEEN® 60, available from "ATRASPOWDER"], a polyoxyethylene castor oil derivative [polyethylene glycol (PEG)-60 hydrogenated castor oil sold under the trademark NIKKOL™ HCO-60, polethylene glycol (PEG)-50 hydrogenated castor oil sold under the trademark NIKKOL™ HCO-50, available from "NIKKO CHEMICALS"]), polyvinylpyrrolidone, polyvinyl alcohol, carboxymethyl cellulose, lecithin, gelatin, hyaluronic acid and the like. Any of those listed above may be employed alone or in combination with each other. The concentration is preferably about 0.0001 to about 10% by weight, more preferably about 0.001 to about 5% by weight.

To the outer aqueous phase, an osmotic agent may be added. This osmotic agent may be any substance giving an osmotic pressure in an aqueous solution thereof.

Such osmotic agent may for example be polyhydric alcohol, monohydric alcohol, monosaccharide, disaccharide, oligosaccharide, amino acid as well as derivatives thereof.

A polyhydric alcohol mentioned above may for example be a trihydric alcohol such as glycerin, a pentahydric alcohol such as arabitol, xylitol and adonitol, a hexahydric alcohol such as mannitol, sorbitol and dulcitol. Among those listed above, a hexahydric alcohol is preferred, with mannitol being especially preferred.

A monohydric alcohol mentioned above may for example be methanol, ethanol and isopropyl alcohol, with ethanol being preferred.

A monosaccharide mentioned above may for example be a pentose such as arabinose, xylose, ribose and 2-deoxyribose, a hexose such as glucose, fructose, galactose, mannose, sorbose, rhamnose and fucose, with a hexose being preferred.

An oligosaccharide mentioned above may for example be a trisaccharide such as maltotriose and raffinose and a tetrasaccharide such as stachyose, with a trisaccharide being preferred.

A derivatives of a monosaccharide, a disaccharide and an oligosaccharide described above may for example be glucosamine, galactosamine, glucuronic acid and galacturonic acid.

An amino acid mentioned above may be any L-amino acid, such as glycine, leucine and arginine. L-Arginine is preferred.

Any of these osmotic agents may be employed alone or in combination with each other.

Any of these osmotic agents is used at a concentration giving the osmotic pressure of the outer aqueous phase which is about 1/50 to about 5 times, preferably about 1/25 to about 3 times the osmotic pressure of physiological saline.

A method for removing an organic solvent may be any method known per se or a method in accordance therewith. For example, the organic solvent is evaporated at atmospheric pressure or under incrementally reduced pressure with stirring using a propeller stirrer, a magnetic stirrer or a ultrasonicating machine, or evaporated with adjusting the vacuum level using a rotary evaporator, or evaporated gradually using a dialyzing membrane.

A microcapsule thus obtained is isolated using a centrifugation or a filtration, and any free forms of the physiologically active substance or its salt, the hydroxynaphthoic acid or its salt, a vehicle, an emulsifier and the like deposited on the surface of the microcapsule are washed off several times with distilled water, and then dispersed again in distilled water and lyophilized.

During a manufacturing process, an anti-aggregating agent may be added in order to prevent the aggregation between particles. Such anti-aggregating agent may for example be a water-soluble polysaccharide such as mannitol, lactose, glucose and starches (such as corn starch), an amino acid such as glycine, a protein such as fibrin and collagen. Among these, mannitol is employed preferably.

After a lyophilization, water and the organic solvent contained in the microcapsule can be removed if necessary under reduced pressure by warming while avoiding the fusion between the microcapsules. Preferably, the warming is accomplished at a temperature which is higher slightly than the intermediate glass transition point of a lactic acid-glycolic acid polymer determined by a differential scanning calorimeter with raising the temperature by 10 to 20° C. per minutes. The intermediate glass transition point of a lactic acid-glycolic acid polymer to a temperature higher by about 30° C. than this temperature is the range of the temperature at which the warming is accomplished more preferably. Preferably, the warming is accomplished at a temperature within the range from the intermediate glass transition point of a lactic acid-glycolic acid polymer to a temperature which is higher than the intermediate glass transition point by 10° C., more preferably at a temperature within the range from the intermediate glass transition point to a temperature which is higher than the intermediate glass transition point by 5° C.

While the time period of the warming may vary depending on the amount of a microcapsule and the like, it is usually about 12 hours to about 168 hours, preferably about 24 hours to about 120 hours, especially about 48 hours to about 96 hours after the temperature of the microcapsule itself reached a certain temperature.

A method for warming is not limited particularly, as long as it enables a uniform warming of a microcapsule bulk.

Such warming method may for example be a method for warming and drying in a thermostat chamber, a fluidized tank, a mobile tank or a kiln, or a method for warming and drying with a microwave. Among these methods, a method for warming and drying in a thermostat chamber is preferred.

(ii) W/O/W Method (1)

First, a solution of a lactic acid-glycolic acid polymer or its salt in an organic solvent is preferred. The organic solvent and the concentration of the lactic acid-glycolic acid polymer or its salt in the organic solvent are similar to those described in the above-mentioned (I)(I). When an organic solvent mixture is employed, the ratio is also similar to that described in the above-mentioned (I)(i).

To a solution of the lactic acid-glycolic acid polymer or its salt in an organic solvent thus obtained, a physiologically active substance or its salt is added and dissolved or dispersed. Then the resultant organic solvent solution (oil phase) containing a composition consisting of the physiologically active substance or its salt and the lactic acid-glycolic acid polymer or its salt is combined with a solution of a hydroxynaphthoic acid or its salt [in the solvent such as water, an aqueous solvent such as an alcohol (e.g., methanol, ethanol), an aqueous solution of pyridine, an aqueous solution of dimethylacetoamide]. The mixture is emulsified by a known method for example using a homogenizer or a ultrasonication to form a W/O emulsion.

Then the resultant W/O emulsion consisting of the physiologically active substance or its salt, the hydroxynaphthoic acid or its salt and the lactic acid-glycolic acid polymer or its salt is added to an aqueous phase to form a W(inner aqueous phase)/O(oil phase)/W(outer aqueous phase) emulsion, and then the solvent in the oil phase is evaporated to prepare a microcapsule. The volume of this outer aqueous phase is usually about 1 to about 10,000 times, more preferably about 5 to about 5,000 times, especially about 10 to about 2,000 times the volume of the oil phase.

An emulsifier and an osmotic agent which may be added to an outer aqueous phase described above and the subsequent preparation are similar to those described in the above-mentioned (I)(i).

(iii) W/O/W Method (2)

First, a solution of a hydroxynaphthoic acid or its salt and a lactic acid-glycolic acid polymer or its salt in an organic solvent is prepared, and the resultant organic solvent solution is referred to as an oil phase. This production method is similar to that described in the above-mentioned (I)(i). Alternatively, the hydroxynaphthoic acid or its salt and the lactic acid-glycolic acid polymer or its salt may be formulated separately into organic solvent solutions, and thereafter the both are mixed. While the concentration of the lactic acid-glycolic acid polymer in an organic solvent solution may vary depending on the molecular weight of the lactic acid-glycolic acid polymer and the type of the organic solvent, it is usually about 0.5 to about 70% by weight, more preferably about 1 to about 60% by weight, especially about 2 to about 50% by weight, when using dichloromethane as an organic solvent.

Then a solution or a dispersion of a physiologically active substance or its salt [in the solvent such as water and a mixture of water and an alcohol (e.g., methanol, ethanol)] is prepared.

The concentration at which the physiologically active solution or its salt is added is usually 0.001 mg/ml to 10 g/ml, more preferably 0.1 mg/ml to 5 g/ml, particularly 10 mg/ml to 3 g/ml.

Known solubilizer and stabilizer may be added. For dissolving or dispersing the physiologically active substance and the additives, heating, shaking or stirring may be performed as long as the activity is not lost, and the resultant aqueous solution is referred to as an inner aqueous phase.

The inner aqueous phase and the oil phase obtained as described above is emulsified by a known method for example using a homogenizer or a ultrasonication to form a W/O emulsion.

The volume of the oil phase to be mixed is usually about 1 to about 1,000 times, more preferably about 2 to about 100 times, especially about 3 to about 10 times the volume of the inner water phase.

The resultant W/O emulsion is usually about 10 to about 10,000 cps, preferably about 100 to about 5,000 cps at about 12 to about 20° C.

Then the resultant W/O emulsion consisting of the physiologically active substance or its salt, the hydroxynaphthoic acid or its salt and the lactic acid-glycolic acid polymer or its salt is added to an aqueous phase to form a W(inner aqueous phase)/O(oil phase)/W(outer aqueous phase) emulsion, and then the solvent in the oil phase is evaporated or diffused into the outer aqueous phase, whereby preparing a microcapsule. The volume of this outer aqueous phase is usually about 1 to about 10,000 times, more preferably about 5 to about 50,000 times, especially about 10 to about 2,000 times the volume of the oil phase.

An emulsifier and an osmotic agent which may be added to an outer aqueous phase described above and the subsequent preparation are similar to those described in the above-mentioned (I)(i).

(II) Phase Separation Method

When a microcapsule is prepared by this method, a coacervating agent is added portionwise with stirring to a solution of a composition consisting of a pharmacologically active substance or its salt, a hydroxynaphthoic acid or its salt and a lactic acid-glycolic acid polymer or its salt in an organic solvent described in the in-water drying method of the above-mentioned (I) to precipitate and solidify the microcapsule. Such coacervating agent is about 0.01 to about 1,000 times, preferably about 0.05 to about 500 times, particularly about 0.1 to about 200 times the volume of the oil phase.

A coacervating agent is not particularly limited as long as it is a polymeric, mineral or vegetable compound miscible with an organic solvent and it does not allow a complex of a physiologically active substance or its salt with a hydroxynaphthoic acid or its salt and a lactic acid-glycolic acid polymer or its salt to be dissolved. Those exemplified typically are silicon oil, sesame oil, soybean oil, corn oil, cottonseed oil, coconut oil, linseed oil, mineral oils, n-hexane, n-heptane and the like. Any of these substance may be employed alone or in combination with each other.

The microcapsule thus obtained is isolated, washed repetitively for example with heptane to make the composition consisting of the pharmacologically active substance or its salt, the hydroxynaphthoic acid or its salt and the lactic acid-glycolic acid polymer or its salt free of the coacervating agent and other material, and then dried under reduced pressure. Alternatively, the washing is performed by the method similar to that described in the in-water drying method in the above-mentioned (I)(i), and then a lyophilizaiton followed by a drying with warming is performed.

(III) Spray-Drying Method

When a microcapsule is prepared by this method, a solution comprising a pharmacologically active substance or its salt, a hydroxynaphthoic acid or its salt and a lactic acid-glycolic acid polymer or its salt in an organic solvent described in the in-water drying method of the above-mentioned (I) is sprayed via a nozzle into a drying chamber of a spray drier, whereby evaporating the organic solvent in a microparticulate droplet within an extremely short period to prepare a microcapsule. Such nozzle may for example be a dual-fluid nozzle, a pressure nozzle, a rotating disc nozzle and the like. Subsequently, the washing is performed if necessary by the method similar to that described in the in-water drying method in the above-mentioned (I) and then a lyophilizaiton followed by a drying with warming is performed.

A microcapsule dosage form other than the microcapsule described above can be prepared by subjecting a solution comprising a pharmacologically active substance or its salt, a hydroxynaphthoic acid or its salt and a lactic acid-glycolic acid polymer or its salt in an organic solvent described in the in-water drying method of the above-mentioned microcapsule production method (I) for example to a rotary evaporator, where the organic solvent and water are evaporated into dryness with controlling the vacuum level, followed by a pulverization using a jet mill and the like, whereby obtaining a fine powder (also referred to as a microparticle).

Thereafter, the pulverized fine powder may be washed by the method similar to that described in the in-water drying method in the above-mentioned microcapsule production method (I) and then a lyophilizaiton followed by a drying with warming is performed.

A microcapsule or a fine powder obtained here enables a medicament release corresponding to the degradation rate of a lactic acid-glycolic acid polymer employed.

A sustained release composition according to the invention may be any dosage form such as a microsphere, a microcapsule, a fine powder (microparticle) and the like, it is preferably in the form of a microcapsule.

A sustained release composition according to the invention can be formulated as it is or employed as a starting material to produce any of various dosage forms, such as an intramuscular, subcutaneous or tissue injection or implantation formulation, a nasal, rectal and intrauterine mucosal formulation, an oral formulation (e.g., solid dosage form such as capsule including hard and soft capsules, granule and powder, liquid formulation such as syrup, emulsion and suspension) and the like.

When a sustained release composition according to the invention is formulated into an injection formulation, it is formulated into an aqueous suspension together with a dispersing agent (e.g., surfactant such as Tween 80 and HCO-60, polysaccharide such as sodium hyaluronate, carboxymethyl cellulose, sodium arginate and the like), a preservative (e.g., methylparaben, propylparaben), an isotonic agent (e.g., sodium chloride, mannitol, sorbitol, glucose, proline), or dispersed together with a vegetable oil such as sesame oil and corn oil to prepare an oily suspension, whereby obtaining a practically utilizable sustained release injection formulation.

The particle size of a sustained release composition when employed as a suspension injection formulation becomes acceptable when it allows the dispersing performance and the passage through the syringe needle to be satisfactory, and the mean particle size may for example be about 0.1 to about 300 μm, preferably about 0.5 to about 150 μm, more preferable about 1 to about 100 μm.

An aseptic formulation of a sustained release composition according to the invention can be obtained for example by a method in which the entire manufacturing process is performed aseptically, a method utilizing a sterilization with a gamma ray or a method in which a preservative is added, although there is no particular limitation.

Since a sustained release composition according to the invention has a low toxicity, it can be used as a safe pharmaceutical in a mammal (e.g., human, cattle, swine, dog, cat, mouse, rat, rabbit).

While the dose of a sustained release composition according to the invention may vary depending on the type and the content of a physiologically active substance as a main ingredient, the dosage form, the duration of the release of the pharmacologically active substance, the target disease and the target animal, it may be an effective amount of the pharmacologically active substance. A single dose of a pharmacologically active substance as a main ingredient, when the sustained release formulation is a 6-month formulation, is preferably about 0.01 mg to about 10 mg/kg body weight a day in an adult, more preferably about 0.05 mg to about 5 mg/kg body weight.

The single dose of a sustained release composition is preferably about 0.05 mg to about 50 mg/kg body weight in an adult, more preferably about 0.1 mg to about 30 mg/kg body weight.

The frequency of the administration may be once in several weeks, once a month or once in several months (e.g., 3, 4 or 6 months), depending on the type and the content of a physiologically active substance as a main ingredient, the dosage form, the duration of the release of the pharmacologically active substance.

While a sustained release composition according to the invention can be used as a prophylactic and therapeutic agent against various diseases depending on the type of the pharmacologically active substance contained therein, it, when containing an LH-RH derivative as a pharmacologically active substance, can be used as a prophylactic and therapeutic agent against a hormone-dependent disease, especially a sex hormone-dependent cancer (e.g., prostate cancer, uterine cancer, mammary cancer, pituitary cancer and the like), a sex hormone-dependent disease such as prostate hyperplasia, endometriosis, hysteromyoma, precocious puberty, dysmenorrhea, amenorrhea, premenstrual syndrome, multilocular ovarian syndrome and the like, and useful as a contraceptive (or against infertility when utilizing a rebound effect after discontinuation). It is also useful for treating a benign or malignant tumor which is not sex hormone-dependent but is LH-RH sensitive.

EXAMPLES

The present invention is further described with referring to the following Examples and Experiments, which are not intended to restrict the invention.

Example 1

A solution of 1.2 g of the acetate of 5-oxo-Pro-His-Trp-Ser-Tyr-DLeu-Leu-Arg-Pro-NH—$C_2H_5$ (hereinafter abbreviated as Peptide A, Takeda Chemical Industries, Ltd.) dissolved in 1.2 ml of distilled water was mixed with a solution of 4.62 g of a DL-lactic acid polymer (weight average molecular weight: 40,600, number average molecular weight: 21,800, terminal carboxyl group level: 52.7 μmol/g) and 0.18 g of 1-hyroxy-2-naphthoic acid dissolved in a solvent mixture of 8.25 ml of dichloromethane and 0.45 ml of ethanol, and emulsified using a homogenizer to form a W/O emulsion. Then the W/O emulsion was poured into 1200 ml of a 0.1% (w/w) aqueous solution of a polyvinyl alcohol (EG-40, Nippon Synthetic Chemical Industry Co., Ltd.) which had previously been kept at 15° C., and agitated using a turbine homomixer at 7,000 rpm to form a W/O/W emulsion. This W/O/W emulsion was stirred at room temperature for 3 hours to allow dichloromethane and ethanol to be evaporated or diffused into the outer aqueous layer, and then the oil phase was solidified, sieved through a 75 μm mesh-sized sieve, centrifuged at 2000 rpm for 5 minutes (05PR-22, Hitachi, Ltd.) to precipitate a microcapsule, which was then recovered. The microcapsule was dispersed again in distilled water, centrifuged again, washed to remove free components and then recovered. To the recovered microcapsule was added a small amount of distilled water to disperse again. 0.3 g of mannitol was dissolved therein and then the mixture was lyophilized to obtain a powder. The % recovery as mass of the microcapsule was 46.91%, and the Peptide A content of the microcapsule was 18.7% while the 1-hydroxy-2-naphthoic acid content was 2.57%.

Example 2

A solution of 1.2 g of the acetate of Peptide A dissolved in 1.2 ml of distilled water was mixed with a solution of 4.62 g of a DL-lactic acid polymer (weight average molecular weight: 40,600, number average molecular weight: 21,800, terminal carboxyl group level: 52.7 μmol/g) and 0.18 g of 3-hyroxy-2-naphthoic acid dissolved in a solvent mixture of 7.5 ml of dichloromethane and 0.45 ml of ethanol, and emulsified using a homogenizer to form a W/O emulsion. Thereafter, the mixture was treated similarly to EXAMPLE 1 to obtain a microcapsule powder. The % recovery as mass of the microcapsule was 53.18%, and the Peptide A content of the microcapsule was 17.58% while the 3-hydroxy-2-naphthoic acid content was 2.49%.

Experiment 1

About 45 mg of each microcapsule obtained in EXAMPLES 1 and 2 was dispersed in 0.3 ml of a dispersion medium (0.15 mg of carboxymethyl cellulose, 0.3 mg of polysorbate 80, 15 mg of mannitol dissolved in distilled water), and administered via a 22 G injection needle subcutaneously to a dorsal area of a 7-week old male SD rat. After a predetermined period, the rat was sacrificed and the microcapsule remaining at the administration site was taken out, examined for the Peptide A content, which was divided by the initial content to obtain a % residue, which is shown in Table 1.

TABLE 1

| | % Residue, Peptide A | |
| --- | --- | --- |
| | Example 1 | Example 2 |
| 1 Day | 92.9% | 93.7% |
| 2 Weeks | 74.6% | 78.8% |
| 4 Weeks | 56.0% | 58.0% |
| 8 Weeks | 31.6% | 36.0% |
| 12 Weeks | 28.3% | 32.3% |
| 16 Weeks | 24.5% | 26.8% |
| 20 Weeks | 17.8% | 23.8% |
| 26 Weeks | 12.6% | 15.6% |

As evident from Table 1, both of the microcapsule of EXAMPLE 1 containing 1-hydroxy-2-naphthoic acid and the microcapsule of EXAMPLE 2 containing 3-hydroxy-2-naphthoic acid could contain the pharmaceutically active substance at high concentrations, and exhibited an extremely high suppressed effect on the initial excessive release of the physiologically active substance. Any of these microcapsules accomplished a sustained release of the physiologically active substance at a constant rate over an extremely prolonged period.

Example 3

A solution of 1.2 g of the acetate of Peptide A dissolved in 1.2 ml of distilled water was mixed with a solution of 4.62 g of a DL-lactic acid polymer (weight average molecular weight: 32,000, number average molecular weight: 17,800, terminal carboxyl group level: 72.1 µmol/g) and 0.18 g of 3-hyroxy-2-naphthoic acid dissolved in a solvent mixture of 7.5 ml of dichloromethane and 0.45 m of ethanol, and emulsified using a homogenizer to form a W/O emulsion. Thereafter, the mixture was treated similarly to EXAMPLE 1 to obtain a microcapsule powder. The % recovery as mass of the microcapsule was 51.2%, and the Peptide A content of the microcapsule was 18.05% while the 3-hydroxy-2-naphthoic acid content was 2.42%.

Experiment 2

About 250 mg of the microcapsule obtained in EXAMPLE 3 was dispersed in 1.5 ml of a dispersion medium (0.75 mg of carboxymethyl cellulose, 1.5 mg of polysorbate 80, 75 mg of mannitol dissolved in distilled water), and administered via a 22 G injection needle intramuscularly to a rump area of a beagle. One the other hand, about 125 mg of this microcapsule was dispersed in 0.75 ml of a dispersion medium (0.375 mg of carboxymethyl cellulose, 0.75 mg of polysorbate 80, 37.5 mg of mannitol dissolved in distilled water), and administered via a 22 G injection needle subcutaneously to a rump area of a beagle. After a predetermined period, a blood was taken from a forearm vein and examined for the serum levels of Peptide A and testosterone, which are shown in Table 2.

TABLE 2

| | Peptide A (ng/ml) | Testosterone (ng/ml) |
| --- | --- | --- |
| | Intramuscular administration | |
| 1 Day | 7.33 | 5.31 |
| 2 Weeks | 0.76 | 0.46 |
| 4 Weeks | 0.91 | 0.58 |
| 8 Weeks | 3.65 | 0.25 or less |
| 12 Weeks | 1.56 | 0.25 or less |
| 16 Weeks | 1.14 | 0.25 or less |
| 20 Weeks | 0.59 | 0.25 or less |
| 26 Weeks | 0.53 | 0.25 or less |
| 28 Weeks | 0.48 | 0.25 or less |
| 30 Weeks | 0.33 | 0.26 |
| 32 Weeks | 0.37 | 0.79 |
| 34 Weeks | 0.22 | 1.41 |
| 36 Weeks | 0.14 | 0.94 |
| | Subcutaneous administration | |
| 1 Day | 17.61 | 2.79 |
| 2 Weeks | 0.99 | 1.95 |
| 4 Weeks | 0.62 | 1.50 |
| 8 Weeks | 0.76 | 0.68 |
| 12 Weeks | 1.77 | 0.25 or less |
| 16 Weeks | 1.57 | 0.25 or less |
| 20 Weeks | 1.23 | 0.25 or less |
| 26 Weeks | 1.93 | 0.33 |
| 28 Weeks | 0.35 | 1.59 |
| 30 Weeks | 0.25 | 2.00 |

As evident from Table 2, the blood level of the physiologically active substance was maintained over a period as long as about 26 weeks, during which the testosterone level as an index of the efficacy was kept at a normal level or lower, and then began to recover a normal level over a period of about 28 weeks to 34 weeks in response to the reduction in the blood level of the physiologically active substance. Even when a hydroxynaphthoic acid is contained in the formulation, the physiologically active substance was present stably in the microcapsule for a prolonged period without losing its activity whereby being released sustainedly. It became also evident that the stable efficacy was exhibited regardless of the administration modes.

Example 4

A solution of 86.2 g of a DL-lactic acid polymer (weight average molecular weight: 28,300, number average molecular weight: 14,700, labeling method-based carboxyl group level: 69.2 µmol/g) dissolved in 67 g of dichloromethane and 87.7 g of a solution obtained by dissolving 9 g of 3-hydroxy-2-naphthoic acid in 210 g of dichloromethane and 16.2 g of ethanol were mixed and adjusted at 28.8° C. 219.2 g of this organic solvent solution was weighed and mixed with an aqueous solution of 20.4 g of the acetate of Peptide A dissolved in 18.8 g of distilled water kept at 54.8° C., and the mixture was stirred for 5 minutes to emulsify only crudely, and then emulsified using a homogenizer at 10,000 rpm for 5 minutes to form a W/O emulsion. Then this W/O emulsion was cooled to 12.7° C. and the poured over a period of 5 minutes and 11 seconds into 20 L of a 0.1% (w/w) aqueous solution of a polyvinyl alcohol (EG-40, NIPPON SYNTHETIC CHEMICAL INDUSTRY CO., LTD.) which had previously been kept at 12.7° C., and agitated using HOMOMIC LINE FLOW (TOKUSHUKIKAI) at 9,000 rpm to form a W/O/W emulsion. This W/O/W emulsion was adjusted at 15° C. for 30 minutes, and then stirred without adjusting the temperature for 2 hours and 30 minutes to allow dichloromethane and ethanol to be evaporated or diffused into the outer aqueous layer, and then the oil phase was solidified, sieved through a 75 µm mesh-sized sieve, centrifuged at 2000 rpm continuously (H-600S, KOKUSANENSHINKI) to precipitate a microcapsule, which was then recovered. The recovered microcapsule was dispersed again in a small amount of distilled water, and sieved through a 90 μm mesh-sized sieve. 12.3 g of mannitol was dissolved therein and then the mixture was lyophilized to obtain a powder. The yield as mass of the microcapsule was 84.4 g, which corresponded to the % recovery of 75.7%, and the Peptide A content was 17.8% while the 3-hydroxy-2-naphthoic acid content was 2.5%.

Example 5

A solution of 107.8 g of a DL-lactic acid polymer (weight average molecular weight: 27,700, number average molecular weight: 15,700, labeling method-based carboxyl group level: 69.8 μmol/g) dissolved in 83.9 g of dichloromethane and 110.2 g of a solution obtained by dissolving 7.5 g of 1-hydroxy-2-naphthoic acid in 175.8 g of dichloromethane and 13.5 g of ethanol were mixed and adjusted at 28.2° C. 274.2 g of this organic solvent solution was weighed and mixed with an aqueous solution of 25.6 g of the acetate of Peptide A dissolved in 23.52 g of distilled water kept at 52.4° C., and the mixture was stirred for 5 minutes to emulsify only crudely, and then emulsified using a homogenizer at 10,080 rpm for 5 minutes to form a W/O emulsion. Then this W/O emulsion was cooled to 12.5° C. and the poured over a period of 3 minutes and 42 seconds into 25 L of a 0.1% (w/w) aqueous solution of a polyvinyl alcohol (EG-40, NIPPON SYNTHETIC CHEMICAL INDUSTRY CO., LTD.) which had previously been kept at 13.1° C., and agitated using HOMOMIC LINE FLOW (TOKUSHUKI-KAI) at 7,000 rpm to form a W/O/W emulsion. This W/O/W emulsion was adjusted at 15° C. for 30 minutes, and then stirred without adjusting the temperature for 2 hours and 30 minutes to allow dichloromethane and ethanol to be evaporated or diffused into the outer aqueous layer, and then the oil phase was solidified, sieved through a 75 μm mesh-sized sieve, centrifuged at 2000 rpm continuously (H-600S, KOKUSANENSHINKI) to precipitate a microcapsule, which was then recovered. The recovered microcapsule was dispersed again in a small amount of distilled water, and sieved through a 90 μm mesh-sized sieve. 15.4 g of mannitol was dissolved therein and then the mixture was lyophilized to obtain a powder. The yield as mass of the microcapsule was 105.7 g, which corresponded to the % recovery of 75.8%, and the Peptide A content was 17.8% while the 1-hydroxy-2-naphthoic acid content was 2.8%.

Example 6

A solution of 107.6 g of a DL-lactic acid polymer (weight average molecular weight: 30,800, number average molecular weight: 13,900, labeling method-based carboxyl group level: 66.3 μmol/g) dissolved in 83.3 g of dichloromethane and 109.7 g of a solution obtained by dissolving 7.5 g of 1-hydroxy-2-naphthoic acid in 175 g of dichloromethane and 13.5 g of ethanol were mixed and adjusted at 28.7° C. 274.3 g of this organic solvent solution was weighed and mixed with an aqueous solution of 24.89 g of the acetate of Peptide A dissolved in 23.49 g of distilled water kept at 51.2° C., and the mixture was stirred for 5 minutes to emulsify only crudely, and then emulsified using a homogenizer at 10,070 rpm for 5 minutes to form a W/O emulsion. Then this W/O emulsion was cooled to 12.8° C. and the poured over a period of 4 minutes and 13 seconds into 25 L of a 0.1% (w/w) aqueous solution of a polyvinyl alcohol (EG-40, NIPPON SYNTHETIC CHEMICAL INDUSTRY CO., LTD.) which had previously been kept at 13.3° C., and agitated using HOMOMIC LINE FLOW (TOKUSHUKI-KAI) at 7,000 rpm to form a W/O/W emulsion. This W/O/W emulsion was adjusted at 15° C. for 30 minutes, and then stirred without adjusting the temperature for 2 hours and 30 minutes to allow dichloromethane and ethanol to be evaporated or diffused into the outer aqueous layer, and then the oil phase was solidified, sieved through a 75 μm mesh-sized sieve, centrifuged at 2000 rpm continuously (H-600S, KOKUSANENSHINKI) to precipitate a microcapsule, which was then recovered. The recovered microcapsule was dispersed again in a small amount of distilled water, and sieved through a 90 μm mesh-sized sieve. 15.4 g of mannitol was dissolved therein and then the mixture was lyophilized to obtain a powder. The yield as mass of the microcapsule was 101.9 g, which corresponded to the % recovery of 73.1%, and the Peptide A content was 17.3% while the 1-hydroxy-2-naphthoic acid content was 2.9%.

Experiment 3

About 45 mg of each microcapsule obtained in EXAMPLES 5 and 6 was dispersed in 0.3 ml of a dispersion medium (0.15 mg of carboxymethyl cellulose, 0.3 mg of polysorbate 80, 15 mg of mannitol dissolved in distilled water), and administered via a 22 G injection needle subcutaneously to a dorsal area of a 7-week old male SD rat. After a predetermined period, the rat was sacrificed and the microcapsule remaining at the administration site was taken out, examined for the Peptide A content, which was divided by the initial content to obtain a % residue, which is shown in Table 3.

TABLE 3

| | % Residue, Peptide A | |
| --- | --- | --- |
| | Example 5 | Example 6 |
| 1 Day | 87.0% | 90.5% |
| 1 Week | 80.0% | 83.2% |
| 2 Weeks | 72.3% | 73.5% |
| 4 Weeks | 57.6% | 58.0% |
| 8 Weeks | 48.2% | 46.7% |
| 12 Weeks | 34.5% | 32.8% |
| 16 Weeks | 23.1% | 22.0% |
| 20 Weeks | 14.7% | 13.4% |
| 26 Weeks | 6.1% | 3.3% |

As evident from Table 3, both of the microcapsules of EXAMPLES 5 and 6 containing 1-hydroxy-2-naphthoic acid, which differed in the molecular weight of the lactic acid polymer as a base, could contain the pharmaceutically active substance at high concentration even when each was produced on the scale of about 125 g, and exhibited an extremely high suppressed effect on the initial excessive release of the physiologically active substance. Any of these microcapsules accomplished a sustained release of the physiologically active substance at a constant rate over an extremely prolonged period.

INDUSTRIAL APPLICABILITY

An inventive sustained release composition contains a pharmacologically active substance at a high concentration and suppresses the initial excessive release of this substance, and maintains a stable releasing rate for a prolonged period (preferably about 6 months or longer).

What is claimed is:

1. A method for producing a sustained release composition, comprising removing a solvent from a mixture of
   a pharmacologically active substance or its salt,
   a polymer chosen from lactic acid homopolymers and salts thereof and lactic acid-glycolic acid polymers and salts thereof, and
   a hydroxynaphthoic acid or its salt.

2. The method according to claim 1 which comprises mixing the pharmacologically active substance or its salt with a solution of the polymer or its salt and the hydroxynaphthoic acid or its salt in an organic solvent, dispersing the mixture, and then removing the organic solvent.

3. The method according to claim 1, wherein the pharmacologically active substance or its salt is an aqueous solution containing the pharmacologically active substance or its salt.

4. The method according to claim 1, wherein the salt of the pharmacologically active substance is a salt with a free base or acid.

* * * * *